United States Patent
Walsh

(10) Patent No.: US 6,546,278 B2
(45) Date of Patent: Apr. 8, 2003

(54) GATED FUNCTIONAL MUSCLE IMAGING

(75) Inventor: Edward G. Walsh, Irondale, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/822,067

(22) Filed: Mar. 30, 2001

(65) Prior Publication Data

US 2001/0047130 A1 Nov. 29, 2001

Related U.S. Application Data

(60) Provisional application No. 60/193,567, filed on Mar. 30, 2000.

(51) Int. Cl.$^7$ ................................................ A61B 5/05
(52) U.S. Cl. ...................................... 600/428; 600/413
(58) Field of Search ................................ 600/428, 415, 600/413, 587, 442, 407, 546, 547; 324/307; 307/309

(56) References Cited

U.S. PATENT DOCUMENTS

| | | | | | |
|---|---|---|---|---|---|
| 5,154,178 | A | * | 10/1992 | Shah | 128/653.2 |
| 5,810,731 | A | * | 9/1998 | Sarvazyan et al. | 600/438 |
| 5,899,859 | A | * | 5/1999 | Votruba et al. | 600/415 |
| 6,114,201 | A | * | 11/2000 | Miyazaki | 324/306 |
| 6,236,886 | B1 | * | 5/2001 | Cherepenin et al. | 600/547 |
| 6,334,852 | B1 | * | 1/2002 | Seyl | 600/587 |

* cited by examiner

*Primary Examiner*—Marvin M. Lateef
*Assistant Examiner*—Devaang Shah
(74) *Attorney, Agent, or Firm*—Benjamin Aaron Adler

(57) ABSTRACT

The present invention provides a new imaging method/system for skeletal muscle function assessment. A gating system triggers imaging device such as magnetic resonance scanner to provide reproducible image data at specific force levels and/or joint angular positions. The present invention further provides applications of such method/system in muscle studies and diagnostics.

25 Claims, 4 Drawing Sheets

GATED FUNCTIONAL MUSCLE IMAGING

CROSS-REFERENCE TO RELATED APPLICATION

This non-provisional patent application claims benefit of provisional patent application U.S. Ser. No. 60/193,567 filed Mar. 30, 2000, now abandoned.

BACKGROUND OF THE INVENTION

1. Field of the Invention

The present invention relates generally to the fields of medical devices and tissue imaging. More specifically, the present invention relates to magnetic resonance imaging of skeletal muscle function.

2. Description of the Related Art

Magnetic resonance (MR) imaging is now used in a variety of applications owing to its versatility. In addition to imaging of anatomy, magnetic resonance imaging can be used to assess physiologic function. Examples of such assessments include perfusion and the mechanical function of the heart. In particular, cardiac function is assessed by acquiring images of the heart at specific time points across the cardiac cycle. Proper timing of these acquisitions is achieved through the use of a triggering mechanism based on the electrocardiogram (ECG). The R-wave of the ECG is used to initiate data collection. Data for specific image frames are taken at designated time intervals referenced to the ECG R-wave. Thus, the result is a set of images of the heart as it exists at each selected time point in the cardiac cycle. If the images are played back as a movie loop, the motion of the heart can be observed, and regional contractile deficiencies noted.

A method for quantifying the contractile function of the heart is known as radiofrequency (RF) tagging. In this method, image data readout is preceded by a composite radiofrequency excitation that produces a series of dark parallel lines in the image. These lines result from the selective saturation of tissue within the field of view (FOV). In cardiac imaging, this excitation would be delivered on the R-wave trigger (i.e. at end diastole). Since material points in the tissue have been saturated, the lines are seen during image playback to move with the tissue as the heart contracts. Two such excitations can be used on the R-wave trigger to produce a grid of lines as seen in FIG. 1. An important feature of this method is that such images can be analyzed using automated techniques to track the tag line motion, and thus produce maps of strain and shear, as well as strain and shear rates.

Examples of cardiac function images using radiofrequency tagging are shown in FIG. 1. These images show the left ventricle in cross-section midway between the base and the apex. The image frame on the left shows the heart at end diastole. This frame corresponds to a very short interval following the ECG R-wave, and shows the tag grid that is produced by the twin composite parallel line excitations. The image frame on the right shows the heart at end systole, corresponding to 300 ms following the ECG R-wave. It is clear that the tag lines show the movement of material points in the cardiac muscle resulting from ventricular contraction. Automated algorithms can track the motion of the tag lines to produce maps of myocardial strain, shear, and velocity.

In contrast to cardiac muscle activity, skeletal muscle activity does not possess an inherent periodicity. Therefore, skeletal muscle function is assessed by acquiring images corresponding to specific force levels rather than to specific time points. Thus, instead of using a single gating trigger to initiate a string of readout excitations at regular intervals, each image frame of skeletal muscle imaging is individually triggered. The resulting images would illustrate regional contractile function of muscle as a function of applied force in an isometric exercise. This is preferred to simply having a subject exert a force prior to acquisition, as voluntary contractions are not exactly reproducible. By using a force (and/or joint position) gating mechanism, reproducible and force correlated results can be obtained.

The prior art is deficient in the lack of effective and non-invasive means of imaging skeletal muscle function on a three dimensional basis. More specifically, the prior art is deficient in the lack of effective means of magnetic resonance imaging of skeletal muscle function wherein the magnetic resonance imaging scanner responds to force and/or angular position as a stimulus for acquisition. The present invention fulfills this long-standing need and desire in the art.

SUMMARY OF THE INVENTION

The present invention provides a gating interface that allows an imaging scanner such as magnetic resonance scanner to respond to specific force level and/or angular position as a stimulus for images acquisition. The present invention also incorporates radiofrequency tagging to quantify the movement of regional skeletal muscle. Specifically, the gastrocnemius and soleus muscles were examined in an isometric plantar flexion exercise to examine the relative recruitment patterns of the gastrocnemius and soleus muscles in order to determine the source of phosphorus metabolite level changes observed in non-localized surface coil spectroscopy studies of exercising muscle.

In one embodiment of the present invention, there is provided a method of imaging skeletal muscle by an imaging scanner which is triggered to produce an image of the skeletal muscle by gating pulses triggered in response to specific force levels and/or joint angular positions. The imaging scanner can be, for example, a magnetic resonance scanner, ultrasound scanner or X-ray CT. In general, the gating pulses are generated by a gating interface consisting of force transducer amplification component, filtering component, timers and multiple comparators which are set with a reference voltage corresponding to a specific force level of interest. Alternatively, a single comparitor can be used with a means of selecting the reference voltage for triggering (voltage corresponding to force and/or joint angular position). For regional quantification, the images can be encoded by radiofrequency tagging.

In another embodiment of the present invention, there is provided a skeletal muscle imaging system, comprising a force transducer to provide a load signal; a magnetic resonance scanner; a gating interface that produces gating pulses to trigger the scanner to produce an image of skeletal muscle at specific force levels and/or joint angular positions; and pulse sequences with appropriate triggering commands to permit radiofrequency tagging of the image of skeletal muscle when a selected force level and/or joint position is achieved. The load signal is force-proportional and/or joint position-corresponding. In general, the gating pulses are generated by a gating interface comprises of force transducer amplification component, filtering component, timers and multiple comparators (or a single comparitor with adjustable threshold) which are set with a reference voltage corresponding to a specific force level of interest.

The present invention further provides methods for analyzing muscle force transmission and/or studying muscle injury by applying the method/system disclosed herein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
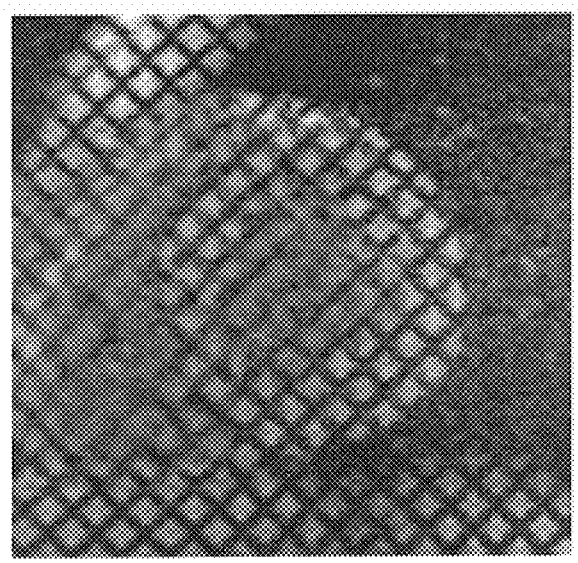
FIG. 1 shows radiofrequency tagged cardiac images taken at end diastole (FIG. 1A) and peak systole (FIG. 1B). The tag lines reflect the motion of the myocardium. Changes in distance between the lines and intersections indicate strain.
Figure 1B:
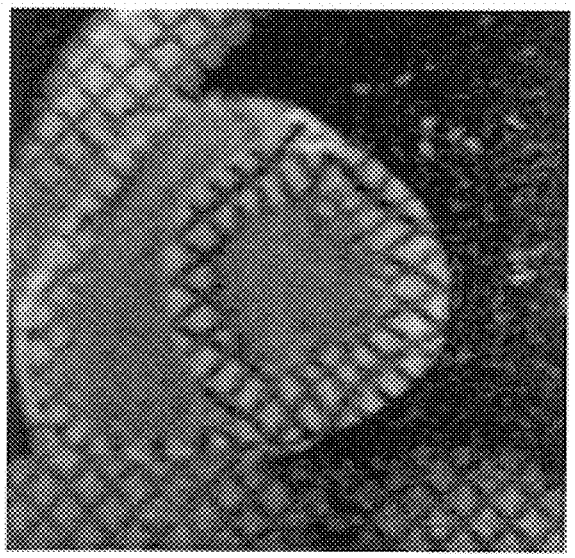

The present invention provides a new imaging process for skeletal muscle function assessment, as well as development of hardware to cause the scanner to produce images at specific force levels and/or joint positions. Specifically, the present invention provides a method by which a scanner such as a magnetic resonance imaging scanner can be triggered to produce images of skeletal muscle corresponding to different force levels, or joint angular position. The actual motion of the muscle tissue is depicted by dark tag lines (radiofrequency tagging) that move with the tissue across the image frame. Such process provides non-invasive image acquisitions that do not require use of ionizing radiation or contrast agents. A full 3-D acquisition of, for example, a leg in under 20 minutes with single slice acquisitions taking less than 30 seconds is anticipated using the imaging process disclosed herein together with recently developed rapid imaging methods.

The present invention features a gating mechanism for activating a scanner based on developed force. This gating mechanism is compatible with a number of transducers, including resistive bridge transducers, and pneumatic pressure transducers. The output of the gating mechanism is a signal that imitates an ECG R-wave (in pulse length and amplitude) permitting attachment of the scanner's ECG leads to the gating mechanism for triggering purposes. Alternatively, pulses corresponding to standard logic levels (TTL, CMOS) can be used to trigger a scanner if so desired. The force thresholds at which trigger pulses are issued can be adjusted by the user according to the imaging protocol to be used. DC bias for the transducer is provided by the gating mechanism through the same front panel connector and multi-conductor cable that carries the transducer output signal to the gating mechanism.

The presently disclosed force-based gating system is expected to be refined with further use of digital techniques, but not to the extent of using microprocessor control.

The gating mechanism can be configured in different embodiments that include one or more of the following features. The gating mechanism may include a variable gain/offset differential amplifier to amplify the small force transducer output signal. The output of the differential amplifier is low-pass filtered to further reduce noise components in the signal. A comparator section compares the amplified force transducer signal to user set thresholds. When a threshold is exceeded, a transistor-transistor logic (TTL) logic pulse is generated. This logic pulse is shaped using an R-C network and attenuated to approximately 5 mV to simulate an ECG R-wave for triggering the scanner. Alternatively, the logic pulse can be applied directly to the gating port of the scanner if desired. The comparator mechanism is such that trigger pulses are issued when a threshold is passed, either as the signal is increasing, or as it is decreasing. Thus, muscle function can be examined during contraction or relaxation.

To sense joint position, motion is coupled to a variable resistor incorporated into a bridge circuit, or as part of a feedback loop of an operational amplifier, to which a DC reference level is applied as signal input. The same comparitor mechanism is then used for threshold gating. In the case of joint position and force, two comparitor mechanims are used with outputs fed to an AND gate such that trigger pulses are issued only when both position and force criteria have been satisfied.

The gating mechanism thus defines the necessary equipment for biasing force or pressure transducers, receiving force or pressure transducer signals and providing trigger signals at appropriate user-defined points in an isometric or isotonic exercise. The disclosed method/device can be used in medical imaging studies such as magnetic resonance imaging or spectroscopy, ultrasound, or x-ray (including computed topography).

Possible applications include muscle and tendon injury studies and diagnosis (such as labral tears in the rotator cuff, quadriceps muscle function following knee ligament repair, etc.), studies of anatomic and functional predispositions to injury in sports and exercise, analysis of muscle function in aging process as well as monitoring of therapeutic interventions. Furthermore, the present invention can aid in sports equipment design and determine the effects of implants on muscle function and motion.

In the present invention, the following terms have the definitions set below.

As used herein, "radiofrequency (RF) tagging" shall refer to the process of selectively saturating tissue magnetization to produce a grid of dark lines for tracking tissue motion.

As used herein, "phase velocity imaging method" shall refer to an MR imaging technique in which gradient pulses are used to sensitize the image acquisition to motion. Signal phase shifts correspond to tissue velocity. Pixel intensities in the resulting phase reconstructed images thus correspond to velocity of tissue represented by each pixel.

As used herein, "radiofrequency shield" shall refer to conductive screening to isolate the scanner bore and electronics from outside electrical interference.

As used herein, "gating interface" shall refer to a device which synchronizes scanner image acquisition to some stimulus.

As used herein, "force-based NMR scanner gating system" shall refer to a gating interface which causes MRI scanner acquisition to take place at user-selected force levels.

As used herein, "gating pulse" shall refer to the digital pulse output by the gating interface which is accepted by the MRI scanner as clearance to acquire image data.

As used herein "force levels" shall refer to those force levels of exercise which have been selected for image acquisition.

As used herein, "joint angular position" shall refer to the angle formed by the bones connected by a given joint under examination.

As used herein, "a force transducer (i.e., a load cell)" shall refer to a device which produces a voltage which is reproducibly proportional to an applied force.

As used herein, "sagittal image" shall refer to an image acquired from a vertical tomographic plane representing the long axis of the body.

As used herein, "tagging excitation" shall refer to the string of radiofrequency and gradient pulses which produce the parallel bands of dark lines in the images.

As used herein, "image readout excitation" shall refer to the string of radiofrequency and gradient pulses which produces the spatially encoded MRI signals for image formation.

As used herein, "isometric exercise" shall refer to exercise in which force is generated but there is not net movement of a joint or limb (isotonic exercise represents motion with constant force).

As used herein, "dynamic imaging" shall refer to imaging of motion.

As used herein, "echo time" shall refer to the time between delivery of the readout excitation radiofrequency pulse and the center of the signal which is acquired from the tissue.

As used herein, "DC bias" shall refer to the direct current signal which is supplied to the load cell.

In one embodiment of the present invention, there is provided a method for imaging skeletal muscle in a subject, comprising the step of applying a imaging scanner to the subject, wherein the scanner is triggered to produce an image of skeletal muscle function by gating pulses supplied at specific force levels and/or joint angular positions. Specifically, the gating pulses are supplied by a force-based gating system which comprises multiple comparators and timers, wherein each comparator and timer corresponds to a force level of interest. For each comparator, there exists a pre-set reference voltage corresponding to each force level of interest. When a load signal rises above or falls below the reference voltage, the comparator produces gating pulses. Preferably, the image is depicted by radiofrequency tagging. More preferably, the force levels are in the range of from about 0 kg to about 200 kg. The gating interface produces a logic gating pulse output compatible with transistor-transistor logic or complementary metal oxide semiconductor logic for scanner gating. The gating interface can also supply a gating pulse that mimicks an ECG R-wave that can be fed to a scanner's ECG monitor for triggering if the scanner is so equipped.

In another embodiment of the present invention, there is provided a skeletal muscle imaging system, comprising a force transducer to provide a load signal; a magnetic resonance scanner; a gating interface that produces gating pulses to trigger the scanner to produce an image of skeletal muscle at specific force levels and/or joint angular positions; and pulse sequences with appropriate triggering commands to permit radiofrequency tagging of the image of skeletal muscle when a selected force level and/or joint position is achieved. Preferably, the load signal is force-proportional and/or joint position-corresponding. The means to trigger the scanner is a force-based magnetic resonance scanner gating system consisting of multiple comparators and timers that correspond to a force level of interest. For each comparator, there exists a pre-set reference voltage corresponding to each force level of interest. When a load signal rises above or falls below the reference voltage, the comparator produces gating pulses to trigger the scanner. Alternatively, a single comparator with adjustable threshold voltages is used.

The present invention further provides methods for analyzing muscle force transmission and/or studying muscle injury by applying the method/system disclosed herein. For example, the present invention is directed to a method for studying muscle injury in a subject, comprising the step of: applying the skeletal muscle imaging system of the present invention to said subject so that muscle and/or tendon injury can be evidenced by an abnormally high rate of strain development as a function of increasing force. Further, the present invention is directed to a method of determining muscle function in individual suffering from abnormal muscle function, comprising the step of: applying the skeletal muscle imaging system described herein to the subject. In the case of depressed metabolic function, reduced perfusion, or collagen matrix breakdown, low strain rates may be observed. Abnormal muscle function results from physiologic abnormality selected from the group consisting of perfusion, metabolic disorder, neurologic defect and collagen matrix abnormality.

The following examples are given for the purpose of illustrating various embodiments of the invention and are not meant to limit the present invention in any fashion.

EXAMPLE 1
Design and Function of a Force-Based Gating System

Figure 2:
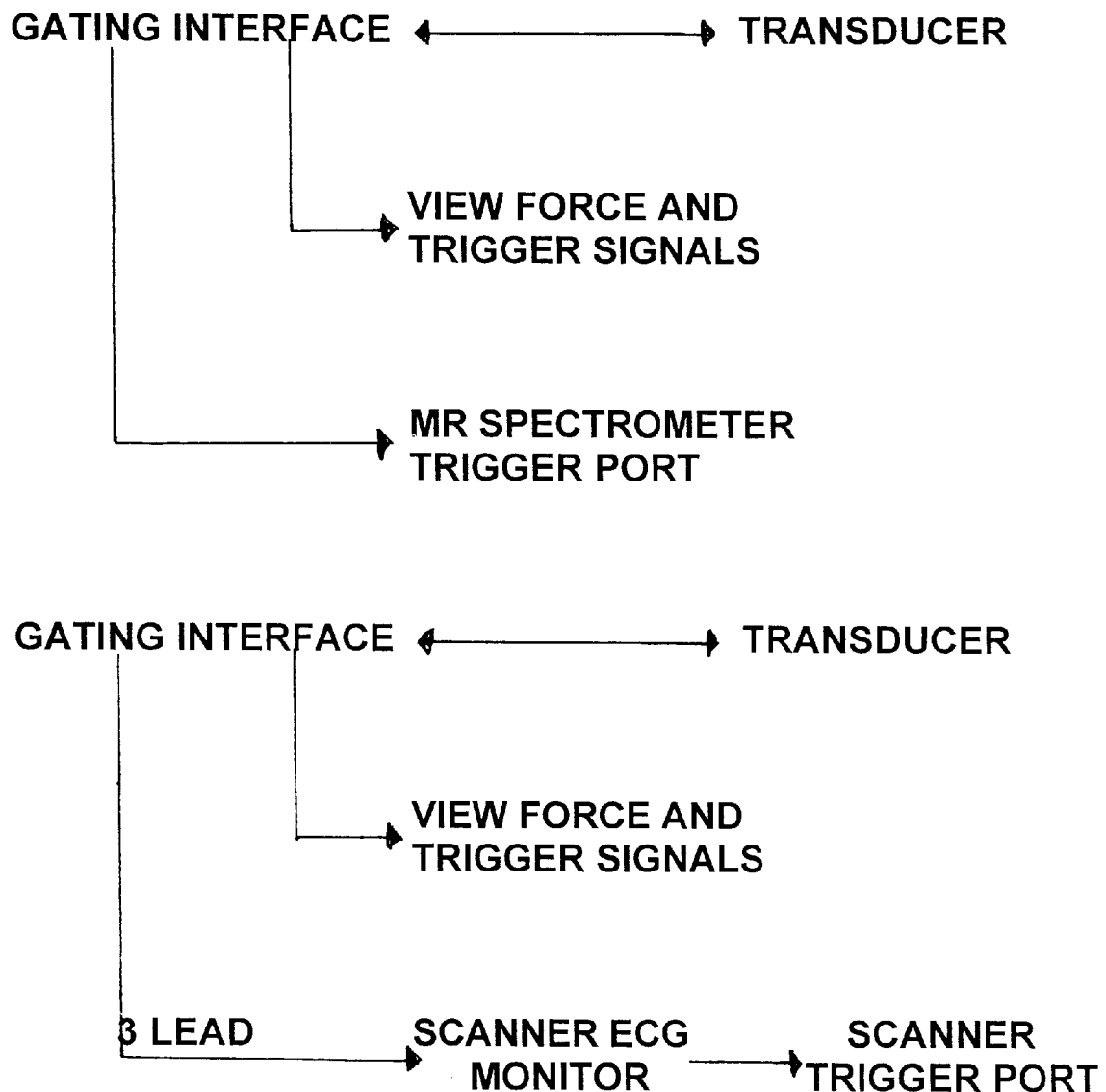
FIG. 2 shows the functional relationship of the components of the muscle imaging system.

For application of radiofrequency (RF) tagging and phase velocity methods in quantitative imaging of skeletal muscle function, it is necessary to generate images corresponding to reproducible levels of muscular force. Use of a force or pressure transducer along with the gating mechanism satisfies the requirements for scanner synchronization to a reproducible physiologic response. The functional relationship of the components is shown in FIG. 2.

There are two possible mechanisms for delivering the trigger signal to the scanner. One approach is to generate a signal that resembles an ECG R-wave, and thus use the scanner ECG monitor and gating mechanism to trigger the scanner. The advantage of this method is that no additional connections need to be made to the scanner gating circuits that are normally not accessed by clinical users. Alternatively, the TTL gating pulse generated within the gating mechanism can be fed directly to the scanner trigger port in cases where ECG monitoring/gating is not available.

Figure 3:
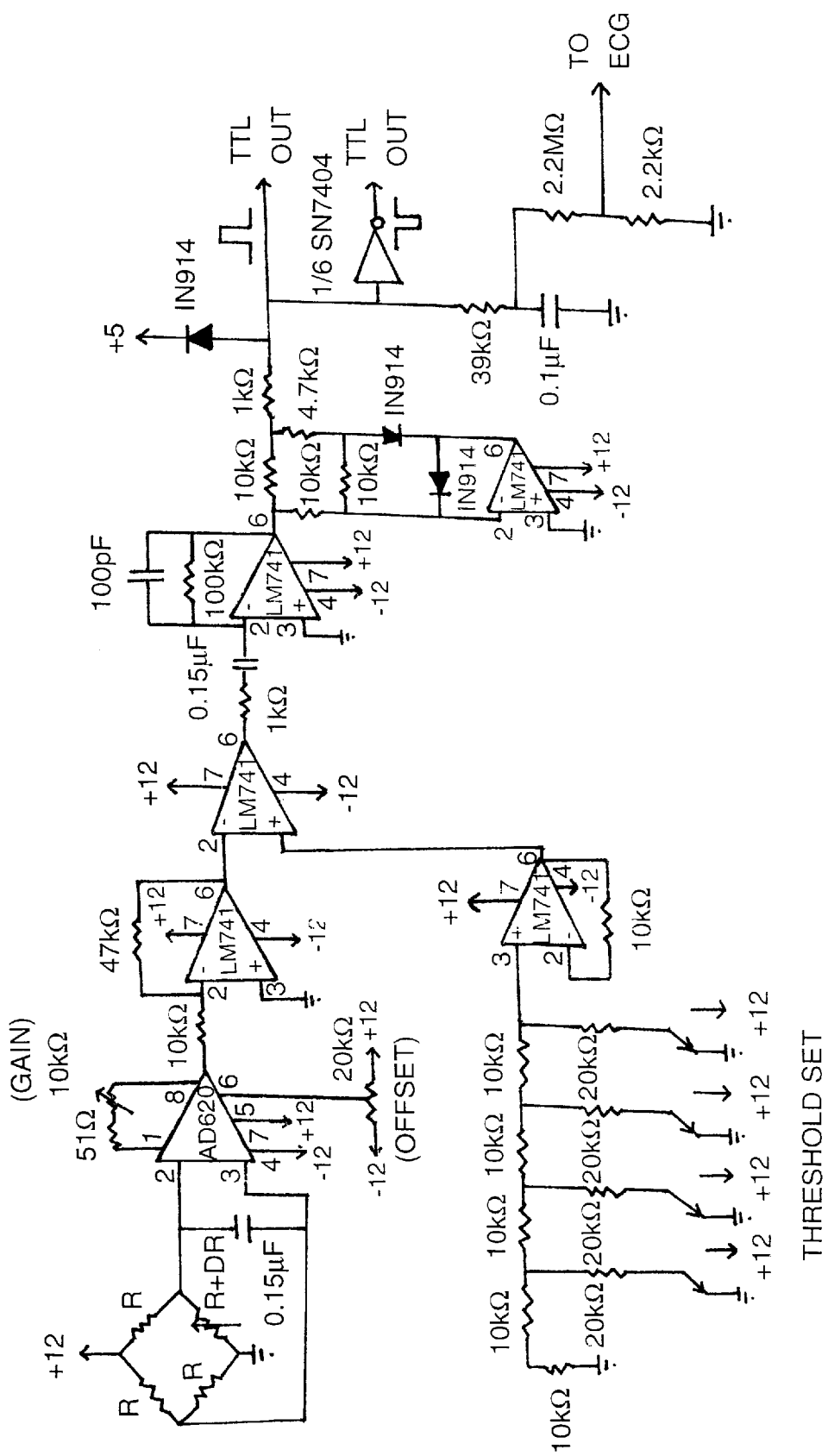
FIG. 3 shows a circuit diagram of the gating interface for scanner triggering.
Figure 4:
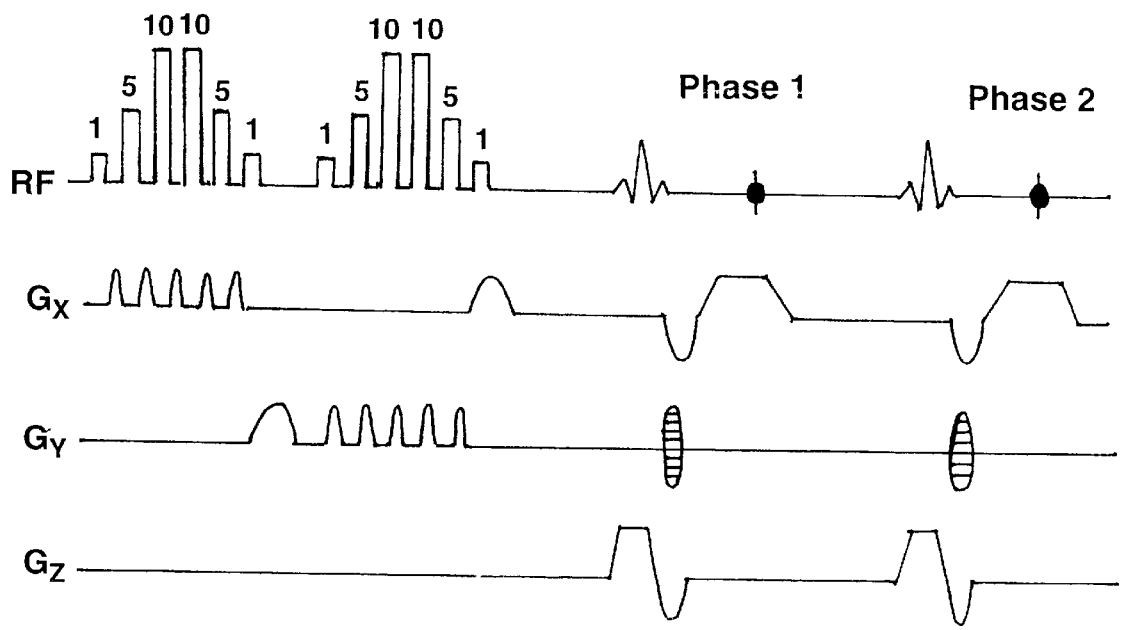
FIG. 4 shows the pulse sequence for radiofrequency tagging. Each group of pulses (with binomial intensity distribution) produces a series of parallel lines perpendicular to the direction of the applied gradient. Two such excitations delivered with both inplane gradients produce a grid pattern as seen in the images of FIG. 1. The binomial excitations are followed by a series of image readout excitations at regular time intervals across the cardiac cycle. The sequence is synchronized to begin with the ECG R-wave.

A force transduction mechanism is illustrated in FIG. 3. In a typical resistive load cell, a bridge circuit is used in which one leg of the bridge consists of a conductor that deflects under force, resulting in a very small change in resistance ($\Delta R$). The resistances of the other three legs of the bridge are fixed in value (R). A DC bias voltage ($V_s$) is applied across the bridge. When the variable leg consisting of a foil or wire is stretched within its elastic limit, its resistance given by:

$$R = \rho(l/A)$$

(where R is the resistance, ρ is the wire or foil resistivity, l is the length, and A is the cross section area) will change. This resistance change results in a voltage at the output of the bridge given by:

$$V_O = (V_i \Delta R)/(4R + 2\Delta R)$$

$V_O$ will be positive or negative depending on the sign of $\Delta R$. Since $\Delta R$ is typically much less than 1%, $V_O$ will typically be on the order of millivolts.

A differential amplifier forms the input stage of the gating mechanism owing to the very small output voltages typically obtained from force and pressure transducers (FIG. 3). A differential amplifier configuration (AD620) is used since the output of the transducer represents a difference between two voltages, both of which are above ground reference. The differential amplifier also offers a high common mode rejection ratio, which is important in reducing effects of 60 Hz and other coherent interferences that can affect signal quality when dealing with small input voltages. Variable gain and DC offset are provided at the differential amplifier stage.

The differential amplifier is followed by a non-inverting operational amplifier (LM741) to provide additional gain as needed. A low pass filter (adjustable cutoff frequency) follows the LM741 to reduce high frequency noise in order to improve the reliability of triggering on signals varying slowly in time. The amplified and filtered transducer signal is made available at a front panel connector to permit viewing of the force waveforms on an oscilloscope, and/or for signal digitization for subsequent analysis. The amplified and filtered signal is fed to a comparator. The reference voltage of the comparator, adjustable by an operator using front panel switches, defines the force levels at which a trigger pulse will be issued both as the force signal increases (increasing muscular force) and decreases (during muscular relaxation). Thus, image acquisition can occur at either contraction or relaxation, or at both relaxation and contraction.

The trigger pulses are available at a front panel connector for viewing along with the force waveform to allow the operator to verify correct operation during scan acquisition. The comparator output is fed to a differentiator circuit to detect the voltage transitions in the output of the comparator, since these transitions occur when the force signal crosses the selected threshold. Since the differentiator output is positive or negative depending on the direction of the comparator output switching, the differentiator output is fed to an absolute value circuit (also known as a precise rectifier). The output of the absolute value circuit is clipped to +5 volts to produce TTL compatible trigger pulses. Thus, trigger pulses are available as the selected threshold is crossed with force either increasing or decreasing. These pulses are made available at the front panel connectors for viewing along with the force signal, and can be fed to a trigger port on the scanner. In addition, the TTL pulses are sent to a 1000:1 voltage divider and RC shaping producing a pulse with a 5 mV amplitude and a 20 ms rise time. This 5 mV (shaped) signal appears across a 2.7 kΩ resistor to simulate correct ECG lead impedance. If the scanner in use is equipped with ECG gating capability, this shaped 5 mV signal can be fed through the ECG leads to trigger the scanner, eliminating the need to connect the gating interface to the scanner trigger port.

EXAMPLE 2
Operation of a Force-Based Magnetic Resonance Imaging System

For isometric exercise, an extremity (e.g. a leg) is exercised against a force transducer (i.e., a load cell). Such a load cell produces a voltage linearly proportional to applied force. The gating system has several functions, such as load cell signal amplification (including variable gain and offset for calibration), low pass filtering for noise reduction to reduce false triggers during slow force change, comparison of amplified transducer voltage with preset thresholds, generation of a scanner-compatible TTL pulse of appropriate duration when a designed force level is reached, and logic inversion (if necessary) for spectrometer compatibility. Additionally, variable load cell amplifier gain and low-pass thresholds are available, as well as the means for generating gating pulses as force increases, or as force both increases and decreases.

In one embodiment in which multiple triggers are required for different force levels for a single muscular effort, the amplified load cell signal with known dependence on force is simultaneously supplied to all of the comparators in the gating interface. Each comparator is set with a different reference voltage to correspond to a specific force level. As the amplified load cell signal passes the reference voltage for a comparator, the output of the comparator would go to the high logic state and trigger a monostable multivibrator circuit which in turn produces a 5 volt pulse of approximately 20 ms duration. The outputs of the multivibrator circuits (one for each comparator) are fed through TTL combining logic to form a string of pulses as force is applied to the load cell, with such pulses corresponding to the points at which the load cell signal arrives at each reference setting (i.e. for each comparator).

These functions have been implemented in analog electronics in a single enclosure and is powered by an external or internal double-ended DC power supply. A 9-pin connector on the front panel is connected to the load cell to provide the load cell with its DC bias and to accept the force-proportional load signal. Additional connectors are provided to permit observation of the filtered load cell signal and the gating pulses during acquisition, with an additional connectors to deliver gating pulses (either standard logic levels, or ECG level) to the NMR scanner. When in use, the gating system is located near the back of the magnet and is connected through the radiofrequency shield to the load cell which is mounted on an exercise bench located in the magnet bore. Total power consumption (with load cell connected) is approximately 2.3 watts. No electrical connections are made directly to the subject, hence issues of safety (e.g. leakage currents) as related to medical monitoring equipment do not apply. The load cell which has been used for the initial experiments is a Tedea-Huntleigh Model 1250 off-center load cell which carries a maximum rating of 300 kg. Load cell output at 300 kg force is 2 mV per volt of bias (in the present invention, 24 mV for 12 V bias). Maximum deviation from linearity is 0.02%, which is more than adequate for this application.

EXAMPLE 3
Pulse Sequence for Muscle Imaging

The pulse sequence used for muscle imaging differs from that used for cardiac imaging in that for the cardiac example, reception of an R-wave trigger results in the generation of the tagging excitation followed by image data readouts at regular time intervals until the sequence has "played out". Thus, the image acquisition begins with an untriggered tagging excitation. Upon hearing the excitation, the subject carries out the designated exercise (force development, or joint motion) until the selected threshold is reached, at which time the scanner is triggered to acquire the image data. Therefore the rapid single-shot image readout includes a "wait for trigger command" as opposed to the cardiac imaging case in which the tag excitation is triggered, with image readout data free running following the tag excitation. "Single shot" image readouts include FLASH (Fast Low Angle Shot) gradient echo techniques, echo planar techniques, and spiral scan (and similar) techniques.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of skeletal muscle imaging in a subject, comprising the step of:
    applying an imaging scanner to the subject;
    generating gating pulses with a gating interface, said gating interface comprising;
        a force transducer amplification component, said component amplifying a signal from a force transducer, said force transducer signal transduced from a force level applied to the skeletal muscle or transduced from said force level at a selected joint angular position of said skeletal muscle; and
        multiple comparators, each of said comparators comparing said amplified signal to a user-set reference threshold set separately therein; wherein if said reference threshold is passed, said comparator generates said gating pulses; and
    triggering said imaging scanner with said gating pulses to produce an image of the skeletal muscle of the subject at said force level or at said force level at the selected joint angular position.

2. The method of claim 1, wherein said imaging scanner produces an image by magnetic resonance imaging, by ultrasound imaging or by X-ray computed tomography.

3. The method of claim 1, wherein, either independently or in combination, said gating interface further comprises:
    a filtering component,
    at least one timer; wherein said timer(s) produces timing pulses if said reference threshold is passed; or
    an audio and/or visual mechanism for feedback of said force level to the subject during scanning to assist in scan exercise protocol compliance.

4. The method of claim 1, wherein said user-set reference threshold in each of said comparators is a reference voltage.

5. The method of claim 1, wherein as said force transducer signal is increasing, said comparator produces an unambiguous signal when said force transducer signal exceeds the reference voltage of said comparator.

6. The method of claim 1, wherein as said force transducer signal is decreasing, said comparator produces an unambiguous signal when said force transducer signal falls below the reference voltage of said comparator.

7. The method of claim 1, wherein said gating interface produces a logic gating pulse output compatible with transistor-transistor logic or complementary metal oxide semiconductor logic for scanner gating.

8. The method of claim 1, wherein said gating interface produces a gating pulse that is similar in amplitude and duration to an electrocardiogram R-wave delivered by surface electrocardiogram electrodes, wherein said pulse can be delivered to the electrocardiogram monitor of a magnetic resonance imaging scanner to permit use of the existing electrocardiogram triggering interface for scanner control during functional skeletal muscle imaging.

9. The method of claim 2, wherein said magnetic resonance imaging is radiofrequency tagged magnetic resonance imaging or phase velocity magnetic resonance imaging.

10. The method of claim 1, wherein said image of skeletal muscle is analyzed using automated techniques to produce data selected from the group consisting of spatial mapping of strain, strain rate, shear, shear rate, velocity, and stress in single dimensions.

11. The method of claim 1, wherein said force level is from about 0 kg to about 200 kg.

12. A skeletal muscle imaging system, comprising:
    a force transducer to provide a load signal;
    a magnetic resonance scanner;
    a gating interface that produces gating pulses to trigger said scanner to produce an image of skeletal muscle at specific force levels and/or joint angular positions, wherein said gating interface is connected to said force transducer through a radiofrequency shield of said magnetic resonance scanner; and
    pulse sequences generated from said gating pulses to trigger radiofrequency tagging of said image of the skeletal muscle.

13. The imaging system of claim 12, wherein said load signal is force-proportional and/or joint position-corresponding.

14. The imaging system of claim 10, wherein said gating interface comprises:
    a force transducer amplification component,
    a filtering component,
    multiple comparators, each of said comparators having a user-set reference threshold with which to compare said load signal wherein if said reference threshold is crossed said comparators produce said gating pulses; and
    timers, said timers producing a timing pulse if said reference threshold is crossed.

15. The imaging system of claim 12, wherein said user-set reference threshold in each of said comparators is a reference voltage.

16. The imaging system of claim 12, wherein as the load signal is increasing, said comparator produces an unambiguous signal when said load signal exceeds the reference voltage of said comparator.

17. The imaging system of claim 12, wherein as the load signal is decreasing, said comparator produces an unambiguous signal when said load signal falls below the reference voltage of said comparator.

18. The imaging system of claim 12, wherein said gating interface further comprises an audio and/or visual mechanism for feedback of force level to a subject during scanning to assist in scan exercise protocol compliance.

19. The imaging system of claim 12, wherein said gating interface produces a logic gating pulse output compatible with transistor-transistor logic or complementary metal oxide semiconductor logic for scanner gating.

20. The imaging system of claim 12, wherein said gating interface produces a gating pulse that is similar in amplitude and duration to an electrocardiogram R-wave delivered by surface electrocardiogram electrodes, wherein said pulse can be delivered to the electrocardiogram monitor of a magnetic resonance imaging scanner to permit use of the existing electrocardiogram triggering interface for scanner control during functional skeletal muscle imaging.

21. The imaging system of claim 12, wherein said image of skeletal muscle is analyzed using automated techniques to produce data selected from the group consisting of spatial mapping of strain, strain rate, shear, shear rate, velocity, and stress in single dimensions.

22. A method for analyzing muscle force transmission in a subject, comprising the steps of:
  applying the skeletal muscle imaging system of claim 14 to said subject before muscle force exertion to produce a pre-exertion image of said muscle;
  applying said skeletal muscle imaging system to said subject during muscle force exertion to produce an exertion image of said muscle; and
  comparing said exertion image with said pre-exertion image, wherein differences in said images provide analysis of muscle force transmission.

23. A method for studying muscle injury in a subject, comprising the step of:
  applying the skeletal muscle imaging system of claim 12 to said subject so that muscle and/or tendon injury can be evidenced by an abnormally high rate of strain development as a function of increasing force.

24. A method of determining muscle function of an abnormally functioning muscle in a subject, comprising the step of:
  applying the skeletal muscle imaging system of claim 14 to said subject.

25. The method of claim 21, wherein said muscle functions abnormally because of a physiological abnormality selected from the group consisting of perfusion, metabolic disorder, neurologic defect and collagen matrix abnormality.

* * * * *